United States Patent
Sartain et al.

(10) Patent No.: US 7,127,951 B2
(45) Date of Patent: Oct. 31, 2006

(54) ROLL FIRMNESS MEASURING SYSTEM AND PROCESS

(75) Inventors: Kevin Sartain, Broken Arrow, OK (US); Nathan Harris, Appleton, WI (US); Steve Wojcik, Mosinee, WI (US); Rick Urquhart, Broken Arrow, OK (US); Mike Daniels, Neenah, WI (US); James Baggot, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/704,384

(22) Filed: Nov. 7, 2003

(65) Prior Publication Data

US 2005/0097966 A1  May 12, 2005

(51) Int. Cl.
*G01N 3/08* (2006.01)
(52) U.S. Cl. ........................................ 73/818
(58) Field of Classification Search .............. 73/82, 73/78, 81, 818; 162/205; 702/42; 115/159.1
See application file for complete search history.

(56) References Cited

U.S. PATENT DOCUMENTS

| | | | |
|---|---|---|---|
| 3,540,270 A | 11/1970 | Wolfer | |
| 3,822,588 A * | 7/1974 | Knight et al. | 73/81 |
| 3,949,537 A | 4/1976 | Jason et al. | |
| 3,958,390 A | 5/1976 | Pringle, Jr. et al. | |
| 4,159,760 A | 7/1979 | Kovacs et al. | |
| 4,430,844 A | 2/1984 | James | |
| 4,594,880 A | 6/1986 | Murdoch et al. | |
| 4,676,094 A | 6/1987 | Hoffmann et al. | |
| 4,765,474 A | 8/1988 | James | |
| 4,866,984 A | 9/1989 | Houghton | |
| 4,875,328 A | 10/1989 | Meyer | |
| 4,883,233 A | 11/1989 | Saukkonen et al. | |
| 4,970,895 A | 11/1990 | Houghton et al. | |
| 5,079,728 A | 1/1992 | Adams et al. | |
| 5,150,850 A | 9/1992 | Adams | |
| 5,195,300 A | 3/1993 | Kovacs et al. | |

(Continued)

FOREIGN PATENT DOCUMENTS

EP   1138620 A2   10/2001

(Continued)

OTHER PUBLICATIONS

Product Information on Veltron (Horizontal/Fill/Seal Machine) from Hayssen Packaging Technologies, 2 pages.

(Continued)

*Primary Examiner*—Edward Lefkowitz
*Assistant Examiner*—Octavia Davis
(74) *Attorney, Agent, or Firm*—Dority & Manning, P.A.

(57) ABSTRACT

An online roll firmness measurement system is disclosed. In one embodiment, a contact element is placed in a fixed position. A roll of material is placed in between the contact element and a support surface. Based upon the amount of force exerted on the contact element, the firmness of the roll of material may be measured. In an alternative embodiment, the contact element applies a predetermined amount of force on the roll of material but is displaced when a roll of material is placed in between the contact element and the support surface. In this embodiment, the amount of displacement of the contact element is measured which allows for the calculation of roll firmness. In one embodiment, a roll firmness device made in accordance with the present invention may be placed in a system for winding rolls and used to maintain rolls of material being formed within preset roll firmness ranges.

24 Claims, 4 Drawing Sheets

U.S. PATENT DOCUMENTS

| | | | |
|---|---|---|---|
| 5,228,273 A | 7/1993 | Kovacs | |
| 5,282,382 A | 2/1994 | Fiore et al. | |
| 5,301,793 A | 4/1994 | Kovacs | |
| 5,402,673 A | 4/1995 | Weinert et al. | |
| 5,433,063 A | 7/1995 | Kovacs et al. | |
| 5,437,417 A | 8/1995 | Kammann | |
| 5,529,563 A * | 6/1996 | Veith et al. | 493/395 |
| 6,077,590 A | 6/2000 | Archer et al. | |
| 6,098,371 A | 8/2000 | Cassoli et al. | |
| 6,161,678 A | 12/2000 | Cassoli et al. | |
| 6,308,497 B1 | 10/2001 | Cassoli et al. | |
| 6,494,399 B1 | 12/2002 | Rautakorpi | |
| 6,684,610 B1 | 2/2004 | Gorrieri et al. | |
| 6,684,611 B1 | 2/2004 | Cassoli | |
| 6,718,728 B1 | 4/2004 | Antoniazzi et al. | |
| 6,755,940 B1 * | 6/2004 | Lin et al. | 162/205 |
| 6,896,767 B1 * | 5/2005 | Wilhelm | 162/117 |
| 2003/0115773 A1 | 6/2003 | Lin et al. | |
| 2003/0231318 A1 | 12/2003 | Sartain et al. | |
| 2004/0068966 A1 | 4/2004 | Hassi | |

FOREIGN PATENT DOCUMENTS

| | | | |
|---|---|---|---|
| EP | 1138620 A3 | 10/2001 | |
| WO | WO 9315008 A1 | 8/1993 | |
| WO | WO 9724595 A1 | 7/1997 | |
| WO | WO 0008253 A1 | 2/2000 | |

OTHER PUBLICATIONS

Product Information on RT 1800 (Horizontal Form/Fill/Seal Machine) from Hayssen Packaging Technologies, 2 pages.

Product Information on Casmatic Casmatic High Speed Bundler B202SP from KPL Packaging, 3 pages www.kpl.net.

Product Information on Casmatic Multibundle CMB 150 from KPL Packaging, 2 pages www.kpl.net.

Product Information on Casmatic Bundler Multibundle CMB202 from KPL Packaing, 2 pages www.kpl.net.

Literature Summary from Hayssen Packaging Technologies, 3 pages www.hayssen.com.

European Search Report for EP04256653.9 Feb. 18, 2005.

Search Report and Written Opinion for PCT/US2005/025568 Nov. 18, 2005.

* cited by examiner

ROLL FIRMNESS MEASURING SYSTEM AND PROCESS

BACKGROUND OF THE INVENTION

In the manufacture of paper products, such as tissue products, a wide variety of product characteristics must be given attention in order to provide a final product with the appropriate blend of attributes suitable for the product's intended purposes. Improving the softness of tissues is a continuing objective in tissue manufacture, especially for premium products. Softness is a perceived property of tissues comprising many factors including thickness, smoothness and fuzziness.

Many tissue products and other paper webs are typically formed into large supply rolls after being manufactured. After the supply rolls are formed, the rolls are rewound into smaller sized rolls, which are generally more useful for commercial purposes. For example, in conventional systems, a core is often placed onto a mandrel that is capable of spinning so that the spinning of the mandrel in conjunction with the core can effectuate winding of the paper thereon.

When tissue products, however, are formed into a rolled product during winding and converting, the inner layers of the rolled product may tend to lose a noticeable amount of bulk due to the compressive forces that are exerted on the base web. Lowering bulk can reduce the perceived quality of the product. As such, a need currently exists for a process and system that controls the winding process in order to control bulk reduction.

Another problem experienced in the formation of wound products is in producing multiple rolls of material that all have a diameter and roll firmness within desired limits. Ideally, the rolled products should have a substantially uniform diameter and roll firmness so that there are no consumer noticed differences between the rolls. Further, consumers desire rolled products, especially rolled tissue products, to have a roll firmness within a desired range such that the rolls do not feel too hard or too "mushy".

The ability to form rolled products having a substantially uniform diameter and roll firmness also provide various other benefits during production of the product. For instance, controlling roll firmness can, in some applications, increase throughput efficiency. Further, uniform products can be easier to package, eliminating or reducing packaging delays that may occur if the rolls were formed with irregular properties.

In the past, one method of measuring roll firmness was to use a Kershaw roll firmness tester as described, for instance, in U.S. Pat. No. 6,077,590 to Archer, et al. which is incorporated herein by reference. The Kershaw roll firmness tester is designed to measure the roll firmness of selected individual cut rolls offline. Unfortunately, once measurements are taken, it is sometimes difficult to use the data for modifying process conditions in order to improve the quality of products produced, due to the delay involved in obtaining the measurement.

As such, a need currently exists for a roll firmness device that is capable of measuring the roll firmness of a roll of material shortly after the roll is formed. A need also exists for a system that can automatically make process adjustments based upon online roll firmness measurements.

Definitions

A tissue product as described in this invention is meant to include paper products made from base webs such as bath tissues, facial tissues, paper towels, industrial wipers, food-service wipers, napkins, medical pads, and other similar products.

Figure 5:
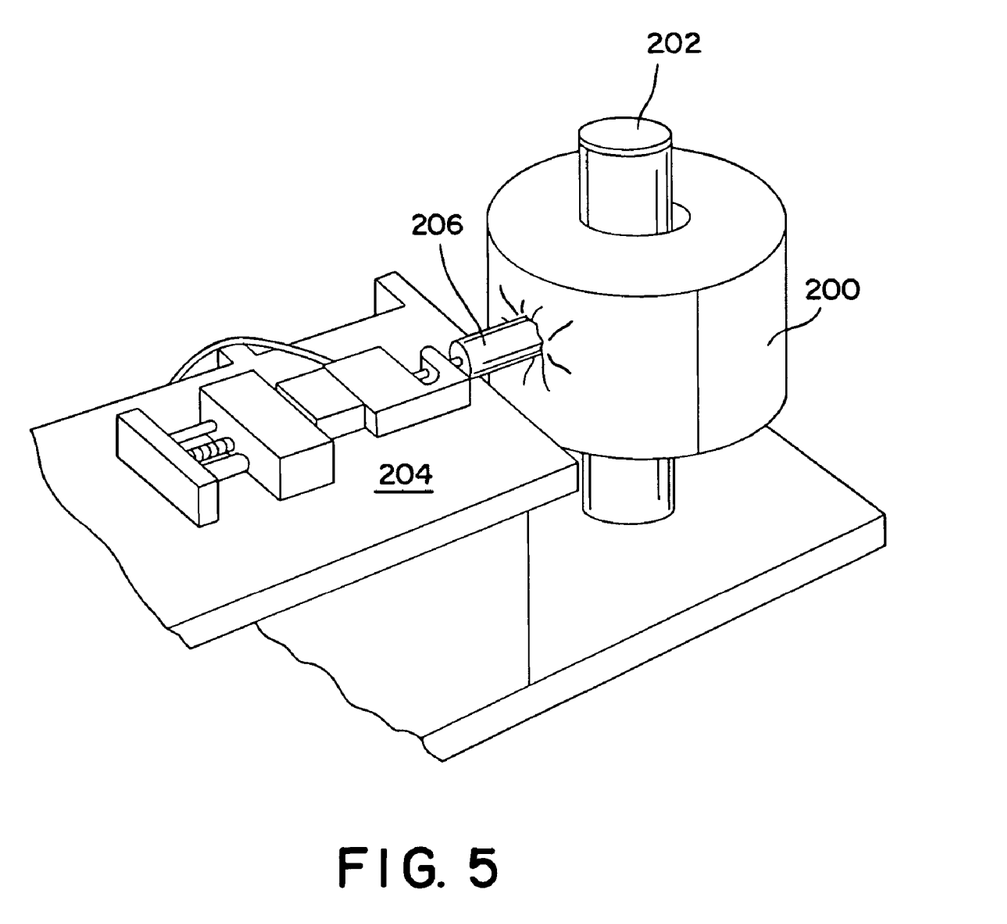
FIG. 5 is a perspective view of a prior art Kershaw roll firmness measurement device.

The Kershaw Test is a test used for determining roll firmness. The Kershaw Test is described in detail in U.S. Pat. No. 6,077,590 to Archer, et al., which is incorporated herein by reference. FIG. 5 illustrates the apparatus used for determining Kershaw roll firmness. The apparatus is available from Kershaw Instrumentation, Inc., Swedesboro, N.J., and is known as a Model RDT-2002 Roll Density Tester. Shown is a towel or bath tissue roll 200 being measured, which is supported on a spindle 202. When the test begins a traverse table 204 begins to move toward the roll. Mounted to the traverse table is a sensing probe 206. The motion of the traverse table causes the sensing probe to make contact with the towel or bath tissue roll. The instant the sensing probe contacts the roll, the force exerted on the load cell will exceed the low set point of 6 grams and the displacement display will be zeroed and begin indicating the penetration of the probe. When the force exerted on the sensing probe exceeds a set point, the value is recorded. After the value is recorded, the traverse table will stop and return to the starting position. The displacement display indicates the displacement/penetration in millimeters. The tester may record this reading. Next the tester will rotate the tissue or towel roll 90 degrees on the spindle and repeat the test. The roll firmness value is the average of the two readings. The test needs to be performed in a controlled environment of 73.4±1.8 degrees F. and 50±2% relative humidity. The rolls to be tested need to be introduced to this environment at least 4 hours before testing.

SUMMARY OF THE INVENTION

The present invention is generally directed to the production of spirally wound products, such as tissue products, that have consumer desired roll bulk and firmness values. The present invention is also directed to a system for producing rolls of material and to online roll firmness measuring devices.

The roll firmness measuring device of the present invention, for instance, in one embodiment applies a contact element against a roll of material that penetrates the roll a fixed distance. The amount of force exerted against the contact element by the roll of material is then recorded. In another embodiment, however, the roll firmness measuring device applies a constant force to a roll of material and the distance a contact element penetrates the roll is recorded.

For example, in the first embodiment, the system of the present invention includes a contact element positioned a predetermined distance from a support surface. The predetermined distance is such that the contact element contacts a roll of material when the roll of material is being supported by the support surface. A force measuring device is used to measure the amount of force exerted against the contact element when a roll of material is placed in between the contact element and the support surface. From the diameter of the roll, the distance between the contact element and the support surface and the amount of force exerted against the contact element by the roll of material, the firmness of a roll can be determined. In one embodiment, for instance, a correlation factor can be used to determine the Kershaw roll firmness.

In one embodiment, the force measuring device can be, for instance, a load cell. A controller, such as a microprocessor, can be placed in communication with the force sensing device for automatically calculating the firmness of a roll.

In calculating the firmness of a roll using the above system, the diameter of the roll of material can be assumed or can be measured. In one embodiment, for example, the system can include a diameter measuring device for measuring the diameter of the roll in conjunction with taking a roll firmness measurement. For instance, the diameter measuring device can comprise a laser spaced from a light sensor. The laser may emit a curtain of light that is intercepted by a roll of material for measuring the diameter of the roll based upon the amount of light sensed by the light sensor. The diameter measuring device, when present in the system, can send information to the controller for use in calculating the firmness of a roll.

In the above embodiment, the contact element is maintained in a fixed position and the amount of force exerted on the contact element when a roll of material is placed on the support surface is measured. In an alternative embodiment of the present invention, however, the contact element can apply a predetermined amount of force against the roll of material and be movable away from the support surface when a force is exerted on the contact element that is greater than the predetermined amount of force that the contact element exerts on the roll of material. The contact element can apply a predetermined amount of force against the roll of material by, for instance, carrying a predetermined amount of weight.

In this embodiment, a displacement measuring device measures the displacement of the contact element from an engagement position to a final position when a roll of material is placed in between the contact element and the support surface. From this information, the firmness of the roll can be calculated.

The displacement measuring device may be, for instance, a potentiometer. A controller, in this embodiment, can also be used to automatically calculate the firmness of a roll by receiving information from a diameter sensing device and the displacement measuring device. In other embodiments, the controller can calculate the firmness of a roll without receiving any information regarding the diameter of the roll. For instance, the diameter of the roll can be assumed to be constant or may not be required if a plurality of contact elements are used on the same roll of material.

Because the system of the present invention is capable of measuring the firmness of a roll of material online or at least close in time to the production of the roll, various open loop or closed loop controls may be added to the system for ensuring that the rolls of material being produced have uniform and desired properties.

For example, in one embodiment, the system of the present invention includes a caliper control device for controlling the caliper of a web of material. A log winding device receives the web of material from the caliper control device and winds the web of material into a roll. In one embodiment, the log winding device can comprise a winding cam and can be programmed to wind the web of material into a roll under determined tension.

A roll firmness device determines a roll firmness value for selected rolls of material wound by the log winding device. A controller, such as a microprocessor, may be in communication with the roll firmness device and the caliper control device. The controller can control the caliper control device in order to selectively increase or decrease the caliper of a web of material based upon the roll firmness value determined from the roll firmness device. For example, the controller can be configured to cause the caliper control device to decrease the caliper of a moving web if the roll firmness value of a previously formed roll is outside a preset limit indicating that the roll is firmer than desired. In a likewise manner, the controller can also be configured to cause the caliper control device to increase the caliper of a moving web if the roll firmness value of a previously formed roll is outside a preset limit indicating that the roll is less firm than desired.

Through the system and process of the present invention, rolls of material having desired characteristics may be repeatedly produced. The process includes the steps of winding a web of material into a roll having a known diameter. The roll of material is then placed on a support surface and a known load is applied to a surface of the roll of material at a known distance from the support surface. From this information, a roll firmness value may be calculated. Based upon the calculated roll firmness value, a caliper control device may then be adjusted for selectively increasing or decreasing the caliper of the web of material prior to being wound into a roll.

Other objects and features of the present invention are discussed in greater detail below.

BRIEF DESCRIPTION OF THE DRAWINGS

A full and enabling disclosure of the present invention, including the best mode thereof to one of ordinary skill in the art, is set forth more particularly in the remainder of the specification, including reference to the accompanying figures in which.

Repeated use of reference characters in the present specification and drawings is intended to represent the same or analagous features or elements of the present invention.

DETAILED DESCRIPTION OF THE INVENTION

It is to be understood by one of ordinary skill in the art that the present discussion is a description of exemplary embodiments only, and is not intended as limiting the broader aspects of the present invention, which broader aspects are embodied in the exemplary construction.

In general, the present invention is directed to a process and system for producing layered sheet products. The layered sheet products may include stacked products and wound products of, for instance, facial tissues, bath tissues, paper towels, wet wipes, industrial wipers, and the like. For instance, the present invention is particularly well suited to the construction of spirally-wound tissue products, such as paper towels and bath tissues. Through the process and system of the present invention, layered products having substantially uniform and desired characteristics may be produced. For example, through the system of the present invention, spirally-wound products may be formed that have a diameter and a roll firmness within desired parameters. The capability of producing roll products having uniform characteristics provides various advantages. For instance, by producing products with uniform properties, process throughput efficiency is increased.

More particularly, the present invention is directed to a firmness measurement device that is capable of measuring the firmness, such as the roll firmness, of a multi-layered product either online or shortly after the product is formed. In the past, roll firmness was generally measured offline on selected rolled products at a relatively slow pace. Consequently, the roll firmness measurements were not available until many further products had already been produced. Further, if the roll firmness values were outside of desired limits, relating the data to winder or raw material conditions was very difficult due to the delay between the winding process and the point at which the roll firmness measurement was taken.

By providing an online roll firmness measurement device, however, roll firmness measurements may be provided immediately after the product is formed allowing for operators to make quick adjustments to the equipment used to form the rolls of product in order to produce uniform products having desired characteristics. In fact, the online roll firmness measurement device of the present invention may be electrically coupled to various pieces of equipment in a closed loop or open loop fashion for making almost instantaneous changes and adjustments in the winding process.

It should be understood, however, that even though the system of the present invention is well suited to producing online roll firmness measurements, the roll firmness device of the present invention need not be placed online. In fact, the system of the present invention may provide various benefits and advantages when used offline as well.

Figure 2:
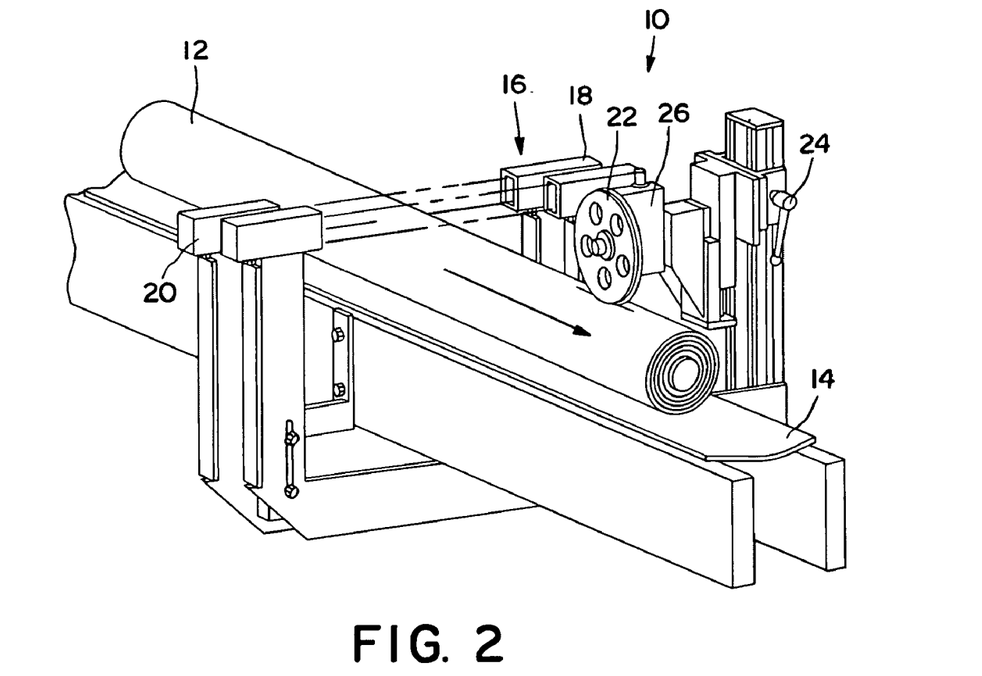
FIG. 2 is a perspective view of one embodiment of a roll firmness device made in accordance with the present invention.

Referring to FIG. 2, one embodiment of a roll firmness device generally 10 made in accordance with the present invention is illustrated. As shown, a roll of material 12 that may have just been formed is forwarded on a support surface to the roll firmness device 10. In this embodiment, the support surface is a moving conveyor 14. It should be understood, however, that in an alternative embodiment, the support surface may be stationary and the roll firmness device 10 may move into contact with the roll of material. Further, instead of a conveyor, the support surface may comprise a mandrel on which the roll is held.

The roll firmness device 10 is shown in conjunction with a diameter measuring device 16 that measures the diameter of the roll of material. In this embodiment, the diameter measuring device 16 includes a pair of focused light sources or lasers 18 and a corresponding pair of light sensors 20 positioned opposite the lasers 18. The lasers 18 emit a curtain of light that is sensed by the light sensors 20. The curtain of light can, for instance, have a width of approximately one inch such as from about 0.8 inches to about 1.2 inches. Further, the curtain of light from each laser is emitted at a particular height with reference to the conveyor 14. When using two lasers as shown in FIG. 2, the lasers may be positioned at different heights in a stepwise manner.

The laser beam that is emitted by the lasers 18 may be non-penetrating beams. Non-penetrating laser beams may be provided, for example, by a gas laser, a solid-state laser, a liquid laser, a chemical laser, a semiconductor laser, and the like.

As shown, when the roll of material 12 is moved on the conveyor 14 adjacent to the diameter measuring device 16, the roll of material intersects the curtains of light being emitted by the lasers 18. Light sensors 20 measure the difference in light intensity caused by the intersection of the light curtains. This information can then be used to determine the diameter of the roll 12. By way of example, the laser beam or beams may have a height of about 24 mm (about 1 inch). Therefore, the diameter of the roll of material is incrementally measurable based on the light sensors 20 receiving from between about 0 to 24 millimeters of the 24 millimeter laser beam. More specifically, a portion of the 24 millimeter laser beam is blocked by the roll of material or log while another portion of the beam is received by the light sensors and converted to the diameter.

Converting the passed-through or received laser beam portion to the diameter is accomplished by the laser assembly which sends, for instance, a 20 milliamp signal to a controller when no portion of the laser beam is being blocked. In other words, the 20 mA signal is produced if the entire 24 mm laser beam is received by the light sensors. Similarly, the laser assembly is configured to send a nominal signal, such as a 4 mA signal to a controller when the laser beam is entirely blocked by the roll of material. Thus, a 4 mA equates to no light being received by the light sensors. In general, the laser beam is adjusted to have a particular height such that half of the beam is blocked when a roll of material at a target diameter is placed on the conveyor. When further rolls of material are placed on the conveyor, the diameter of the roll is determined from the amount of light that is blocked by the roll.

It should be noted that a 4 to 20 milliamp signal, which corresponds to 0 to 24 mm, is by way of example only. For instance, a laser assembly can be provided which uses any suitable milliamp range. Numerous other signal ranges are contemplated to accommodate various lasers from different manufacturers and/or to accommodate specific user requirements.

The diameter measuring device as described above is also disclosed in U.S. patent application Ser. No. 10/172,799 filed on Jun. 14, 2002 to Sartain et al, which is incorporated herein by reference in its entirety.

It should be understood, however, that any suitable diameter measuring device may be used in the system of the present invention. For example, in other embodiments, the diameter measuring device may reflect light off of the top of the roll to measure the diameter of the roll. Optionally, a wheel or roller may make contact with the roll of material for measuring the diameter.

It should also be understood that a diameter measuring device is completely optional. For example, in one embodiment, the system can assume a diameter for a roll of material. In this embodiment, for instance, the diameter of the rolls of material as they are produced may be measured intermittently simply to ensure that the diameter of the rolls of material are within preset limits. Roll firmness measurements as described below may occur based upon a diameter assumption.

As shown in FIG. 2, downstream of the diameter measuring device 16 is a contact element 22 that contacts the roll of material 12. As shown, contact element 22 is a wheel or a roller. In other embodiments, however, a stationery shoe may be used that has a low friction surface. The contact element 22 is maintained a particular distance from the support surface or conveyor 14. This distance may be adjusted manually using a brake device 24. It should be understood, however, that any suitable mechanism may be used in order to adjust the position of the contact element.

As the roll of material 12 passes under the contact element 22, the roll 12 exerts a force against the contact element 22. The amount of force placed against the contact element is measured by a force measuring device 26, such as a load cell. The load cell may be, for instance, in one embodiment a strain gauge. As also shown in FIG. 2, the contact element also displaces into the roll of material 12 as the roll passes below the contact element. The distance the contact element 22 is displaced into the roll of material 12 depends on the diameter of the roll of material and the height of the contact element.

From the diameter of the roll of material 12, the distance between the contact element 22 and the conveyor 14, and from the amount of force measured by the load cell 26, a roll firmness value may be calculated.

In one embodiment, it may be desirable to create a callibration correlation for the roll firmness device prior to use in a process. For example, empirical data may be accumulated and the data can be used to solve the following equation:

$$\frac{1}{\text{Load}} + \frac{1}{\text{Displacement}} + \text{constant} = \text{Roll Firmness}$$

The above empirical equation can then be plotted for forming a curve. This curve may then be used to evaluate any roll firmness value that is later obtained.

If desired, the roll firmness made by the roll firmness device may be correlated into a Kershaw roll firmness value. For example, the Kershaw roll firmness may be calculated in units of distance such as millimeters.

For many products, particularly tissue products, the rolls of materials should have a Kershaw roll firmness within a consumer desired range. In general, the Kershaw roll firmness of a tissue product, for instance, may be between about 6 mm to about 10 mm, and particularly between about 6 mm and about 8 mm.

Through the roll firmness device 10 as shown in FIG. 2, roll firmness values may be calculated shortly after the roll of material 12 is formed, allowing for quick or immediate adjustments to be made during the winding process for maintaining the rolls of material within desired ranges.

In the embodiment illustrated in FIG. 2, the contact element 22 may be maintained at a particular height as rolls of material are carried along the conveyor 14. Alternatively, the contact element 22 may move between an engagement position where the contact element 22 contacts the roll of material and a disengagement position in which the contact element does not contact the roll of material. For example, in one embodiment, when the roll of material 12 is sensed by the diameter measuring device 16, an actuator may be activated causing the contact element 22 to move from a disengagement position to an engagement position for taking a measurement. The actuator can be, for instance, a pneumatic or hydraulic cylinder, a roller screw, or a linear motor. The contact element 22 may move along a linear pathway or may pivot into place. By moving between an engagement position and a disengagement position, the contact element only contacts the roll of material 12 when a roll firmness measurement is desired.

The roll firmness device 10 may take roll firmness measurements at a single location on the roll of material 12 or along the entire length of the roll. By taking multiple roll firmness readings along the length of the roll of material, variations of firmness values within the roll itself may be discovered, which may indicate that the rolls of material are not being wound properly. This data may ultimately be used to improve product consistency and uniformity.

To prevent the contact element 22 from causing damage to the roll of material 12 or to prevent the roll firmness device from being damaged, in one embodiment, the roll firmness device 10 can include a safety release device that releases the contact element from an engagement position when a force exerted against the contact element exceeds a preset limit. When the safety release device is activated, an alarm, such as an audible or visible alarm may also be set off in order to alert an operator.

Figure 3:
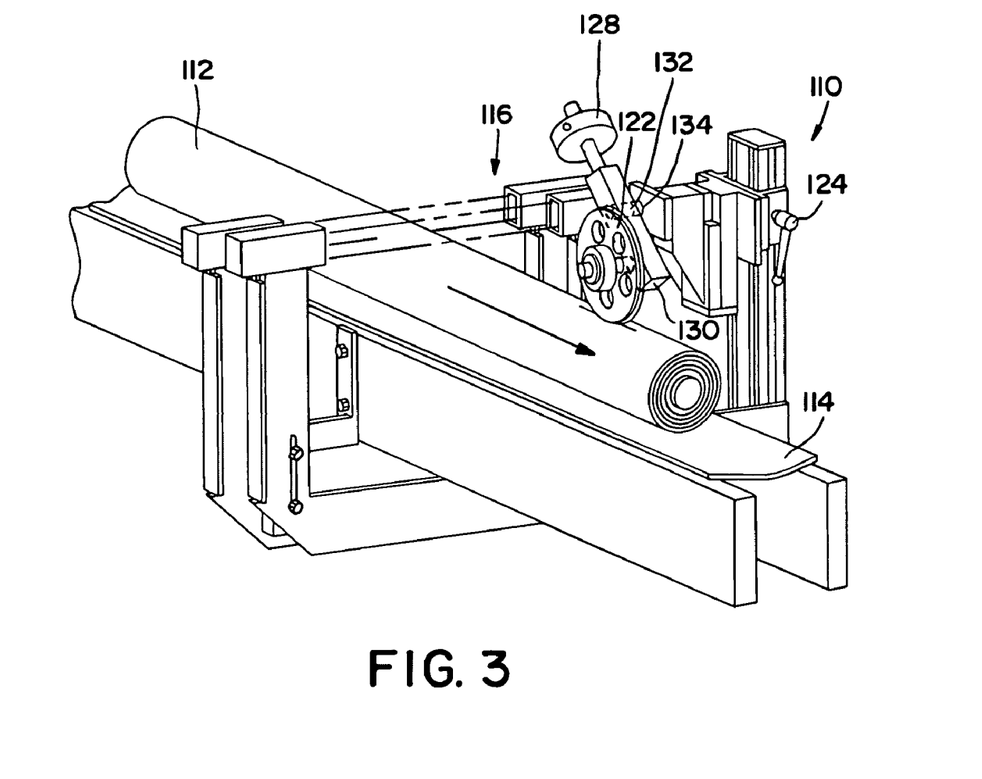
FIG. 3 is a perspective view of another embodiment of a roll firmness device made in accordance with the present invention.

In the embodiment illustrated in FIG. 2, the contact element 22 is placed in a fixed position and a force measuring device 26 measures the amount of force exerted against the contact element when the roll of material is passed below the contact element. Referring to FIG. 3, an alternative embodiment of a roll firmness device generally 110 is shown. In this embodiment, a contact element 122 applies a fixed amount of force to a roll of material 112. The contact element 122 is also movable. The amount of movement or displacement of the contact element 122 is then measured in order to calculate the roll firmness.

More particularly, as shown in FIG. 3, the roll firmness device 110 includes a diameter measuring device 116 similar to the embodiment illustrated in FIG. 2. A roll of material 112 is conveyed on a conveyor 114 into contact with the contact element 122. The contact element 122 is initially placed a predetermined distance from the conveyor 114 that is controlled by a brake 124.

In this embodiment, the contact element 122 is associated with a first weight 128 and a second weight 130. The weights 128 and 130 are selected such that the contact element applies a predetermined amount of force onto the roll of material 112.

As shown, the contact element 122 may pivot about a pivot point 132. When the roll of material 112 is positioned below the contact element 122, the roll of material causes the contact element to pivot a distance away from the conveyor 114. This distance is then measured by a displacement measuring device 134.

The displacement measuring device 134 may be any suitable instrument capable of measuring the displacement of the contact element 122. In one embodiment, for instance, the displacement measuring device 134 may be a potentiometer. Alternatively, a laser may be used to directly measure how much the contact element 122 has displaced into the roll of material 112.

By knowing the diameter of the roll of material 112, the amount of force applied to the roll of material by the contact element 122, and by knowing the amount the contact element displaces when a roll of material is positioned below the contact element, one can calculate a roll firmness value for the roll of material. Similar to the embodiment illustrated in FIG. 2, this roll firmness value may be correlated to a Kershaw roll firmness value.

Thus, in the embodiment illustrated in FIG. 3, a constant force is applied to the roll of material and the displacement of the contact element is measured. The amount of force exerted onto the roll of material 112 by the contact element may be varied as desired. For example, more or less weight may be applied to the contact element. In an alternative embodiment, the contact element may be in operative association with a pneumatic or hydraulic cylinder that applies the predetermined amount of force to the roll of material.

Figure 4:
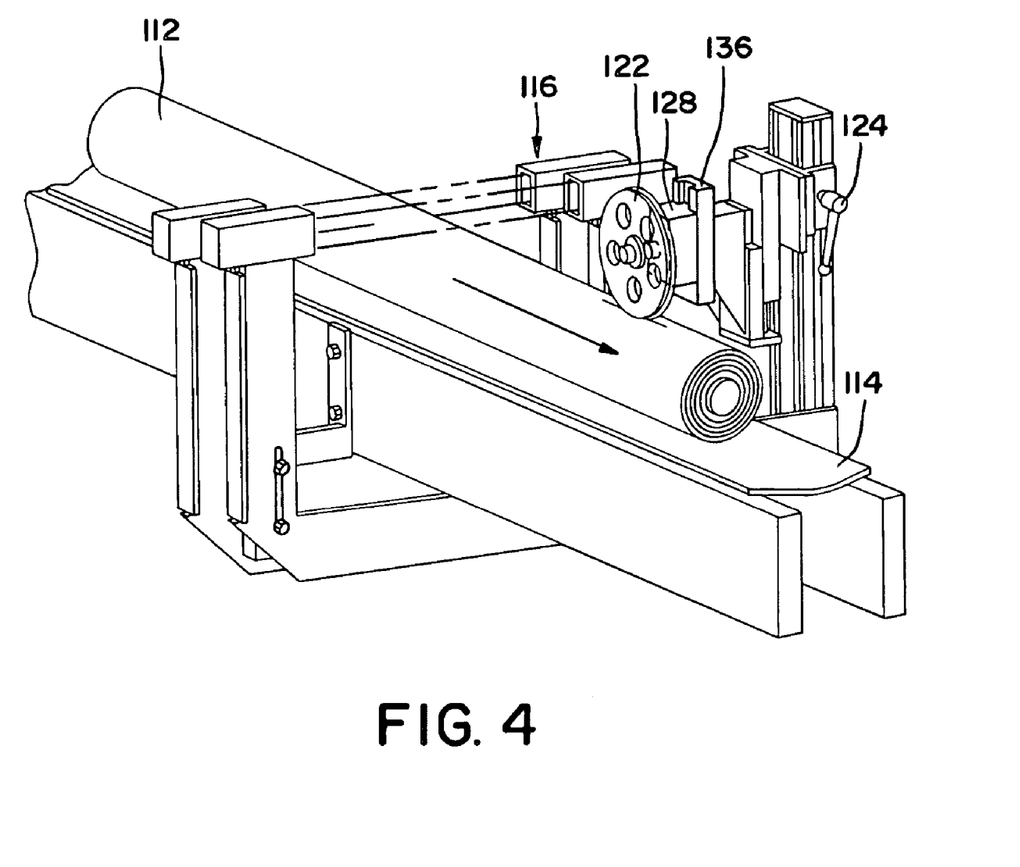
FIG. 4 is a perspective view of still another embodiment of a roll firmness device made in accordance with the present invention.

In the embodiment shown in FIG. 3, the contact element 122 pivots between an engagement position and a final resting position when the roll of material 112 is positioned below the contact element. In an alternative embodiment, however, as shown in FIG. 4, the contact element 122 may be positioned on a linear track 136 that allows the contact element 122 to move up and down. In this embodiment, the contact element 122 is placed in association with a weight 128.

Similar to the description of the embodiment illustrated in FIG. 2, the contact element 122 in FIGS. 3 and 4 may also be connected to an actuator that moves the contact element from an engagement position to a disengagement position. As described above, in this manner, the roll of material 112 is only contacted by the contact element 122 when a measurement is desired.

Since the roll firmness device of the present invention is capable of online roll firmness measurements, the roll firmness device is well suited to being integrated into a winding process. Once integrated into a winding process, roll firmness measurements may be taken as desired and the information obtained from the roll firmness device may be used to control various equipment in the process in order to produce rolls of material having substantially uniform and desirable characteristics.

Figure 1:
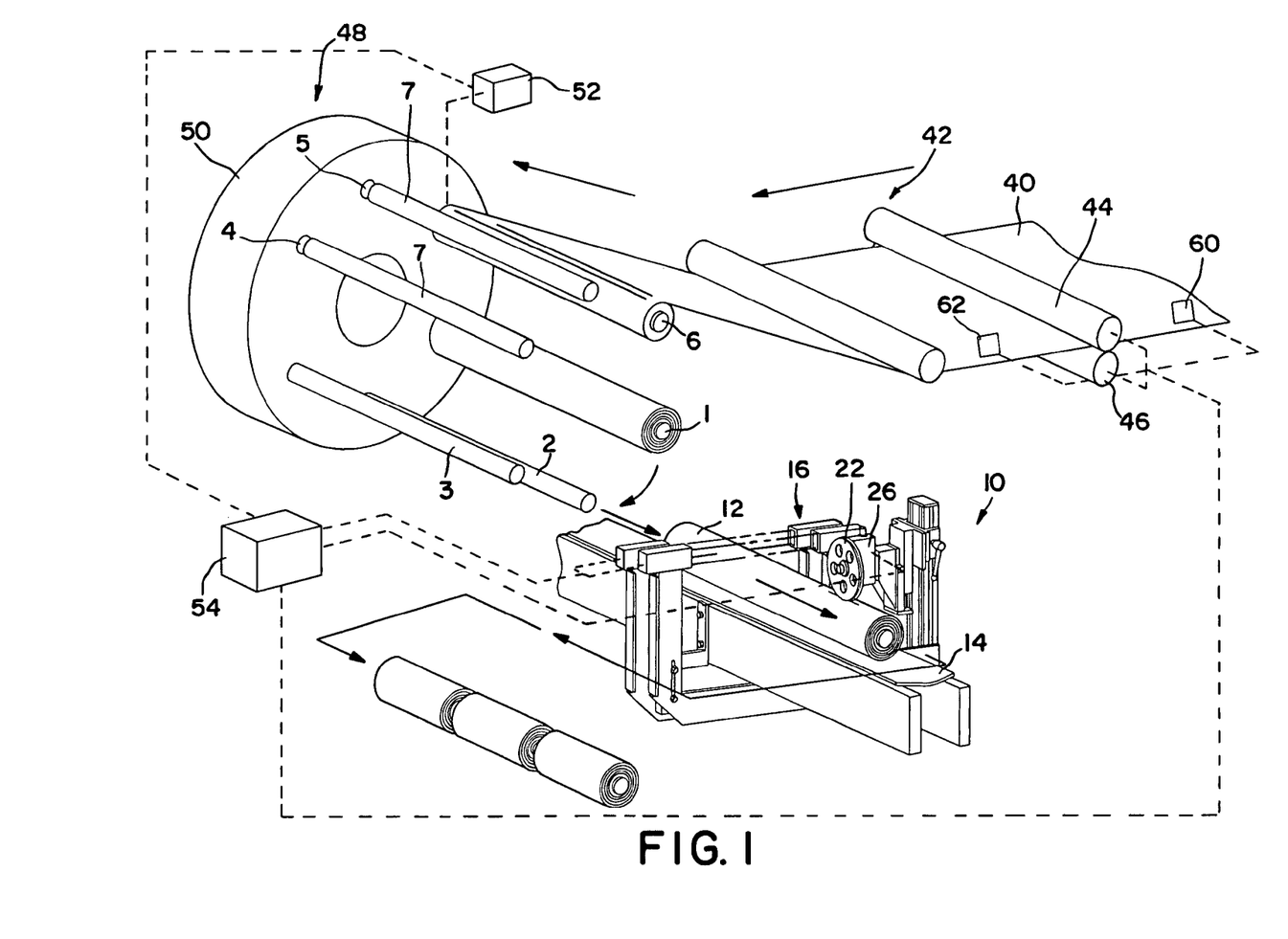
FIG. 1 is a perspective view of one embodiment of a system for producing rolls of material in accordance with the present invention.

For example, one embodiment of a system for forming rolled products is illustrated in FIG. 1. Although the system in FIG. 1 may form rolls of any type of material, the system is particularly well suited for forming paper rolls, such as rolls of bath tissue or paper towels. Such products are typically formed from pulp fibers, have a bulk of at least 2 cc/g, and may have a basis weight of from about 6 gsm to about 120 gsm, such as from about 10 gsm to about 80 gsm.

As shown in FIG. 1, in this embodiment, a web of material 40 is first fed through a caliper control device 42. The caliper control device 42 may be, for instance, a calendering device containing a top roller 44 spaced from a bottom roller 46. The rollers 44 and 46 form a nip through which the web of material 40 is fed. By applying pressure to the web, the thickness or caliper of the web may be reduced.

When using a calendering device, the calendering device may be a gap calendering device or a contact calendering device. Further, the rollers 44 and 46 may be steel rollers, rubber-coated rollers, or mixtures thereof.

In addition to a calendering device, any suitable caliper control device may be used in accordance with present invention. For example, in an alternative embodiment, an embossing device may be used in order to control the caliper of the web. In still another alternative embodiment, the caliper may be controlled by adjusting tension in the web as the web is wound. For example, tension in the web can be increased or decreased using a dancer roll, which are well known in the art.

From the caliper control device 42, the web of material 40 is fed to a log winding device. In general, any suitable long winding device may be used in accordance with the present invention. For instance, the winding device may be a surface winding device, a center winding device, a coreless winding device, and the like.

In the embodiment shown in FIG. 1, the log winding device is incorporated into a turret assembly generally 48. As shown, the turret assembly 48 includes a turret 50 attached to various mandrels. Turret 50 can generally be indexed into a variety of positions during the winding process. For instance, the indexing can occur by rotating the turret 50 about its longitudinal axis. The rotation of the turret can be accomplished by any variety of methods known in the art.

In the embodiment illustrated in FIG. 1, six mandrels 1, 2, 3, 4, 5 and 6 are rotatably affixed to the turret 50. Although the turret assembly 48 is depicted as including six mandrels, it should be understood that only one mandrel or any number of mandrels greater than one can be affixed to the turret 50. In other embodiments, it should be understood that a turret assembly is not needed. For instance, in an alternative embodiment, a surface winder may be used.

The winding process is generally initiated by placing a core 7 onto the mandrel 3 according to any method known in the art. The position of mandrel 3 as shown in FIG. 1 may be described as the "core loading position" of the turret 50. Once the core 7 is placed onto the mandrel 3, the turret 50 can then be indexed into an "adhesive application position", which is the position occupied by mandrel 4 in the embodiment shown. In this position, any suitable adhesive (not shown) can be applied to the core 7 by any method known in the art.

Once an adhesive is applied to the core 7, the turret 50 is once again rotated moving the core into a "prespin position", which is the position occupied by mandrel 5. At the "prespin position", the mandrel can be rotated to ensure that the mandrel achieves a certain rotational speed before the web of material 40 is wound on the core 7. In one embodiment, as shown in FIG. 1, the mandrel 5 can be "prespun" in a counter-clockwise direction.

Once initially rotated at the "prespin position", the mandrel can then be indexed by the turret 50 into a "winding position", which is the position occupied by mandrel 6. The rotational speed of the mandrel imparted at the "prespin position" is generally greater than the feed speed of the web of material 40 such that, as the rotating mandrel is indexed into the "winding position", the web of material 40 can wind around the mandrel. In particular, a leading edge of the web of material 40 contacts the adhesive on the core 7 which secures the web of material to the core as winding continues.

The rotational speed of the mandrel 6 at the "winding position" is controlled by any suitable log winding device, such as a winding cam 52. In one embodiment, for instance, the winding cam 52 may vary the rotational speed of the mandrel 6 as the size of the roll increases in order to maintain the web of material 40 under constant tension.

After the web of material 40 is wound onto the core 7 at the mandrel 6, the mandrel may then be indexed by the turret 50 into a "tail seal and removal position", which is the position occupied by mandrel 1 in the embodiment illustrated in FIG. 1. At the "tail seal and removal position", the end portion of the paper web 40 can be sealed to the roll of material using any suitable sealing device. The sealing device may be configured, for instance, to apply glue or some other adhesive to the end of the web of material such that the tail can be sealed to the roll.

Once the end of the web of material has been sealed, the finished roll 12 may then be removed onto the conveyor 14 as described in FIG. 2. As described above, the conveyor 14 transports the roll of material 12 into contact with the roll firmness device 10. The roll firmness device 10 takes one or more roll firmness measurements. The roll of material 12, if desired, may then be cut into smaller lengths as shown in FIG. 1 and packaged for consumer use.

As shown in FIG. 1, the system of the present invention further includes a controller 54, such as a microprocessor. The controller 54 is placed in communication with a caliper control device 42, the winding device 52, the diameter measuring device 16, and the load cell 26. The controller may be configured, for instance, to calculate a roll firmness value for the roll of material 12 and, based on this information, to then control the caliper control device 42 and/or the winding cam 52 should the diameter of the roll of material 12 or the measured firmness of the roll be outside preset limits. Specifically, the controller 54 can be configured to make adjustments in the thickness of the sheet of material 40 and/or in the amount of tension that is placed upon the web of material during winding. Through the system, the diameter of the rolls of material produced and/or the firmness of the rolls of material produced may be controlled within preset limits such that every roll produced has substantially uniform and desirable characteristics.

For example, in one embodiment, the winding device 52 may be preprogrammed to wind the web of material into a roll according to a particular winding profile. Once the rolls are formed, roll firmness measurements may be made using the roll firmness device 10. A roll firmness value may be calculated by the controller 54. Based upon the calculated roll firmness values, the controller 54 can then be configured to control the caliper control device for selectively increasing or decreasing the caliper of the web of material 40. For example, the controller can be configured to cause the caliper control device to decrease the caliper of the moving Web if the roll firmness measurements are outside a preset limit indicating that the roll is firmer than desired. Similarly, the controller can also be configured to cause the caliper control device to increase the caliper of the moving web 40 if the roll firmness measurements are outside a preset limit indicating that the roll is less firm than desired.

The above process may also be used to maintain the diameter of the rolls of material within preset limits. Through the roll firmness device of the present invention, diameter and firmness adjustments may be made instantaneously instead of being checked periodically as is done currently.

In one alternative embodiment, as shown in FIG. 1, the system of the present invention can further include at least one caliper sensor. For example, the system can include a first caliper sensor 62 positioned after the calendering device 42 and an optional second caliper sensor 60 positioned before the calendering device 42. The caliper sensors 62 and 60 may be used to measure the sheet caliper and to modify the calendering load to produce a constant caliper. The caliper sensors may also be used to correct for changing incoming raw materials or other transient process conditions. In general, any suitable caliper-sensing device known in the art may be used. The caliper sensor 62 and 60, for instance, may determine the caliper of a web mechanically and/or electronically.

When using two caliper sensors as shown in FIG. 1, the downstream caliper sensor 62 may be used to correct caliper in a feedback manner, while the upstream caliper sensor 60 may be used in a feed-forward control. The combination of the readings obtained from the caliper sensors 60 and 62 may allow for the correction of short-term variation in the system. The roll firmness device 10 may then modify the caliper set point to maintain the required firmness as described above.

In one particular embodiment, the caliper sensors 62 and 60 may be used to form a control loop for maintaining a constant caliper. The roll firmness device 10 in conjunction with the controller 54 may then be used to change the caliper set point so that the rolls being produced fall within a target firmness value. In essence, in this embodiment, the system includes two control loops, namely a fast inner loop to control caliper and a slower outer loop to control the resulting firmness. In this embodiment, controller 54 may be used alone or in conjunction with further controllers. For example, a separate controller may be used for the caliper control loop.

In another embodiment of the present invention, the caliper control device 42 may be fixed at a particular position and the controller 54 may be used to make adjustments to the winding device 52 in response to diameter and roll firmness measurements received from the roll firmness device 10.

In still another embodiment of the present invention, the controller 54 can be configured to control the caliper control device 42 and the winding device 52 simultaneously based upon measurements received from the roll firmness device 10.

Through the system of the present invention, as described above, rolls of material can be produced having uniform and desired firmness values and diameters. Various other advantages are also possible through the present invention, however. For instance, the system of the present invention can also be used to control the caliper of the web of material 40 that is presented to the winding device. By controlling the caliper of the web, the amount of tension placed on the web during winding and the roll firmness characteristics of the rolls, the sheet width within the finished rolls is also controlled. If the sheet width within the rolls were irregular, for example, when cut, the material layers contained in the rolls may have a tendency to shift. Further, irregular sheet width within the rolls can also lead to misalignments of a design that has been printed onto the material.

For instance, in some embodiments, designs are printed upon the web of material 40. By producing rolls that have uniform firmness and diameter values, print registration on a cut roll may be improved. In the past, print patterns had a tendency to fall out of alignment when the rolls of material were cut after being wound due to sheet width irregularities. Through the process of the present invention, this problem may be minimized.

In the embodiments shown in the drawings, a conveyor 14 is used to move the rolls of material into contact with the roll firmness measuring device. In other embodiments, however, it should be understood that the roll firmness measuring device may be placed at different locations in the system. For example, in one embodiment, the roll firmness device may be placed adjacent to the mandrel 2. In this embodiment, roll firmness measurements may be taken prior to unloading the roll of material from the mandrel.

In still another embodiment, the roll firmness device of the present invention may be used at other manufacturing locations. For example, the roll firmness device of the present invention is particularly well suited for use during consumer packaging of the rolled products. The roll firmness device may be used online as the products are being packaged or may be set up offline in order to selectively test certain rolls prior to packaging. In this embodiment, for example, the roll firmness device may be used to determine whether a roll has a particular diameter and/or roll firmness suitable for packaging. If the roll does not fall within preset limits, the roll may be discarded or recycled. Further, should one or more rolls fall outside preset limits, a controller may be used to automatically make adjustments to the process line, such as to the packaging equipment, in order to provide corrective feedback.

Irregular rolls may interfere with the packaging of the products, especially when multiple rolls are being packaged in the same container. An irregular sized roll may, for instance, cause the packaging to tear or cause the packaging equipment to malfunction. By using the roll firmness device of the present invention to remove rolls without desired characteristics, packaging delays may be minimized.

The present invention may be better understood with reference to the following example.

EXAMPLE

In this example, a system for measuring the firmness of a roll of material was constructed similar to the apparatus illustrated in FIG. 2. Rolls of SCOTT® paper towels produced by the Kimberly-Clark Corporation were measured using the apparatus in order to develop a calibration correlation for the roll firmness device as described above. Over 70 rolls were measured using the device. The empirical data was plotted in order to solve for the following equation:

$$\frac{1}{\text{Load}} + \frac{1}{\text{Displacement}} + \text{constant} = \text{Roll Firmness}$$

The following result was obtained:

$$\text{Roll Firmness} = \frac{3463.97}{\text{Load Average}} - \frac{35.636}{\text{Displacement Average}} + 6.55078$$

From the above equation, roll firmness values may be established for rolls of material tested by the apparatus. Further, it is believed that the above equation will provide roll firmness data for other types of commercial products tested on the apparatus in addition to the SCOTT® paper towels.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A process for producing rolls of material with uniform characteristics comprising:
    winding a web of material into a roll of material having a known diameter;
    placing the roll of material on a support surface;
    applying a known load to a surface of the roll of material at a known distance from the support surface;
    calculating a roll firmness value and, based on the calculated roll firmness value, adjusting a caliper control device for selectively increasing or decreasing the caliper of the web of material prior to being wound into a roll of material.

2. A process as defined in claim 1, wherein the web of material comprises a paper web.

3. A process as defined in claim 1, wherein the support surface comprises a conveyor.

4. A process as defined in claim 1, wherein the support surface comprises a mandrel.

5. A process as defined in claim 1, wherein the known load is applied to the surface of the roll of material by a contact element, the contact element being positioned a predetermined distance from the support surface, the predetermined distance being such that the contact element contacts a roll of material when the roll of material is supported by the support surface, and wherein the load is known from a force sensing device that measures the amount of force exerted against the contact element when a roll of material is placed in between the contact element and the support surface.

6. A process as defined in claim 1, wherein the known load applied to the surface of the roll of material is applied by a contact element positioned at an engagement position a predetermined distance from the support surface, the predetermined distance being such that the contact element contacts the roll of material when the roll of material is supported by the support surface, the contact element applying a predetermined amount of force against the roll of material, the contact element being movable away from the support surface when a force is exerted on the contact element that is greater than the predetermined amount of force exerted on the roll of material, and wherein a displacement measuring device measures a displacement of the contact element from the engagement position to a final position when the roll of material is placed in between the contact element and the support surface.

7. A process as defined in claim 1, wherein the web of material is wound into a roll by a winding cam, the winding cam winding the web of material into a roll under substantially constant tension.

8. A process as defined in claim 1, wherein the caliper control device is adjusted to decrease the caliper of the web of material if the roll firmness value is outside a preset limit indicating that the roll is firmer than desired, and wherein the caliper control device increases the caliper of the web of material if the roll firmness value is outside a preset limit indicating that the roll is less firm than desired.

9. A process as defined in claim 5, wherein the force sensing device comprises a load cell.

10. A process as defined in claim 6, wherein the displacement measuring device comprises a potentiometer.

11. A process as defined in claim 1, wherein the diameter of the roll of material is known from a diameter measuring device, the diameter measuring device measures the diameter of the roll of material when the roll of material is on the support surface.

12. A process as defined in claim 1, wherein a controller receives the known diameter, the known load, and the known distance from the support surface and calculates the roll firmness value.

13. A process as defined in claim 1, wherein the caliper control device comprises a calendering device.

14. A process as defined in claim 1, wherein the web of material is fed into the process from a parent roll.

15. A process as defined in claim 1, further comprising the step of packaging the rolls of material after the rolls are formed.

16. A process as defined in claim 1, wherein the web of material comprises a tissue product.

17. A process for producing a tissue product comprising:
    winding a tissue web into a roll of material having a known diameter;
    placing the roll of material on a support surface;
    applying a known load to a surface of the roll of material at a known distance from the support surface;
    calculating a roll firmness value and, based on the calculated roll firmness value, adjusting a caliper control device for selectively increasing or decreasing the caliper of the tissue web prior to being wound into a roll of material.

18. A process as defined in claim 17, wherein the tissue web comprises a bathroom tissue.

19. A process as defined in claim 17, wherein the tissue web comprises a paper towel.

20. A process as defined in claim 17, wherein the known load is applied to the surface of the roll of material by a contact element, the contact element being positioned a predetermined distance from the support surface, the predetermined distance being such that the contact element contacts a roll of material when the roll of material is supported by the support surface, and wherein the load is known from a force sensing device that measures the amount of force exerted against the contact element when a roll of material is placed in between the contact element and the support surface.

21. A process as defined in claim 17, wherein the known load applied to the surface of the roll of material is applied by a contact element positioned at an engagement position a predetermined distance from the support surface, the predetermined distance being such that the contact element contacts the roll of material when the roll of material is supported by the support surface, the contact element applying a predetermined amount of force against the roll of material, the contact element being movable away from the support surface when a force is exerted on the contact element that is greater than the predetermined amount of force exerted on the roll of material, and wherein a displacement measuring device measures a displacement of the contact element from the engagement position to a final position when the roll of material is placed in between the contact element and the support surface.

22. A process as defined in claim 17, wherein the caliper control device is adjusted to decrease the caliper of the tissue web if the roll firmness value is outside a preset limit indicating that the roll is firmer than desired, and wherein the caliper control device increases the caliper of the tissue web if the roll firmness value is outside a preset limit indicating that the roll is less firm than desired.

23. A process as defined in claim 17, wherein the diameter of the roll of material is known from a diameter measuring device, the diameter measuring device measures the diameter of the roll of material when the roll of material is on the support surface.

24. A process as defined in claim 17, wherein the caliper control device comprises a calendering device.

* * * * *